United States Patent

Seele et al.

[11] Patent Number: 5,164,408
[45] Date of Patent: Nov. 17, 1992

[54] 1,2-DIHALOAZOLYLETHANE DERIVATIVES AND CROP PROTECTION AGENTS CONTAINING THEM

[75] Inventors: Rainer Seele, Fussgoenheim; Norbert Goetz, Worms; Walter Himmele, Walldorf; Reiner Kober, Fussgoenheim; Wolfgang Rohr, Wachenheim; Eberhard Ammermann, Ludwigshafen; Gisela Lorenz, Neustadt; Wilhelm Rademacher; Johann Jung, both of Limburgerhof, all of Fed. Rep. of Germany

[73] Assignee: BASF Aktiengesellschaft, Ludwigshafen, Fed. Rep. of Germany

[21] Appl. No.: 552,037

[22] Filed: Jul. 13, 1990

[30] Foreign Application Priority Data

Jul. 13, 1989 [DE] Fed. Rep. of Germany ....... 3923151

[51] Int. Cl.$^5$ .................. A01N 43/653; C07D 249/08
[52] U.S. Cl. .................. 514/383; 514/184; 548/101; 548/262.2; 548/267.2; 548/267.8; 548/268.6
[58] Field of Search .................. 548/101, 262.2, 267.2, 548/267.8, 268.6; 514/184, 383

[56] References Cited

U.S. PATENT DOCUMENTS

| | | | |
|---|---|---|---|
| 4,102,891 | 7/1978 | Timmler et al. | 548/262.2 |
| 4,657,921 | 4/1987 | Frick et al. | 548/262.2 |
| 4,715,887 | 12/1987 | Kramer et al. | 548/267.8 |
| 4,783,474 | 11/1988 | Krantz et al. | 514/383 |
| 4,829,074 | 5/1989 | Bushell | 514/359 |
| 5,039,815 | 8/1991 | Seele et al. | 548/262.2 |

FOREIGN PATENT DOCUMENTS 0015756 9/1980 European Pat. Off. .
0195557 9/1986 European Pat. Off. .

OTHER PUBLICATIONS

Burger, "Medicinal Chemistry" 2nd Ed. NY 1960, p. 1055.

Primary Examiner—Patricia L. Morris
Attorney, Agent, or Firm—Oblon, Spivak, McClelland, Maier & Neustadt

[57] ABSTRACT

1,2-Dihaloazolylethane derivatives of the general formula I

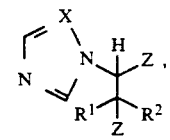

where $R^1$ and $R^2$ are each substituted or unsubstituted phenyl, biphenyl, naphthyl or hetaryl, Z is chlorine or bromine, and X is CH or N, and their plant-tolerated acid addition salts and metal complexes, and fungicides and growth regulators containing these compounds.

6 Claims, No Drawings

1,2-DIHALOAZOLYLETHANE DERIVATIVES AND CROP PROTECTION AGENTS CONTAINING THEM

The present invention relates to novel azolyl compounds, processes for their preparation and growth regulators and fungicides containing them.

It is known that triazole derivatives, for example 2,4′-difluoro-α-(1,2,4-triazol-1-ylmethyl)-benzhydryl alcohol, can be used as a fungicide (European Patent 15,756). However, its fungicidal action is unsatisfactory.

We have found that 1,2-dihaloazolylethane derivatives of the general formula I

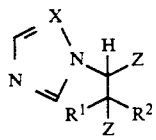

I where
R$^1$ and R$^2$ are identical or different and are each phenyl, biphenyl, naphthyl or hetaryl, and these radicals may be monosubstituted to trisubstituted by halogen, nitro, phenoxy, amino, alkyl, alkoxy or haloalkyl, each of 1 to 4 carbon atoms,
Z is chlorine or bromine and
X is CH or N, and their plant-tolerated acid addition salts or metal complexes have a better fungicidal action than known azole compounds.

The compounds of the formula I contain asymmetric carbon atoms and can therefore occur as enantiomers and diastereomers. In the case of the novel compounds, the mixtures of the diastereomers can be separated in a conventional manner, for example on the basis of their different solubilities or by column chromatography, and the isomers can be isolated in pure form. The racemates of the novel compounds can be resolved by known methods, for example by salt formation with an optically active acid, separation of the diastereomeric salts and liberation of the enantiomers by means of a base.

Both the individual enantiomers or diastereomers and the mixtures thereof can be used as fungicidal and growth-regulating active ingredients.

R$^1$ and R$^2$ are identical or different and are each, for example, 1-naphthyl, 2-naphthyl, p-biphenyl, phenyl, halophenyl, 2-chlorophenyl, 2-fluorophenyl, 2-bromophenyl, 3-chlorophenyl, 3-bromophenyl, 3-fluorophenyl, 4-fluorophenyl, 4-chlorophenyl, 4-bromophenyl, 2,4-dichlorophenyl, 2,3-dichlorophenyl, 2,5-dichlorophenyl, 2,6-dichlorophenyl,2-chloro-6-fluorophenyl, C$_1$–C$_4$-alkoxy-phenyl 2-methoxyphenyl, 3-methoxyphenyl, 4-methoxyphenyl, 2,4-dimethoxyphenyl, C$_1$–C$_4$-alkylphenyl, 4-ethylphenyl, 4-isopropylphenyl, 4-tert-butylphenyl, 4-tertbutoxypheny, 2-chloro-4-fluorophenyl,2-chloro-6-methylphenyl, 3,4-dimethoxyphenyl, 3-phenoxyphenyl, 4-phenoxyphenyl, 3-nitrophenyl, 4-nitrophenyl, 3-aminophenyl, 4-aminophenyl, 2-trifluoromethylphenyl, halo-C$_1$–C$_4$-alkyl-phenyl, 3-trifluoromethylphenyl,4-trifluoromethylphenyl, pyridyl, 3-pyridyl, furyl, 2-furyl, thienyl, 2-thienyl, 3-thienyl, isoxazolyl or 5-isoxazolyl.

Acid addition salts are, for example, the hydrochlorides, bromides, sulfates, nitrates, phosphates, oxalates or dodecylbenzenesulfonates. The activity of the salts is due to the cation, so that the anion is in general unimportant. The novel active ingredient salts are prepared by reacting the 1,2-dihaloazolylethane derivatives (I) with the acids.

Metal complexes of the active ingredients I or of their salts may be formed with, for example, copper, zinc, tin, manganese, iron, cobalt or nickel, by reacting the 1,2-dihaloazolylethane derivatives with corresponding metal salts.

The compounds of the formula I can be prepared, for example, by reacting a compound of the formula II

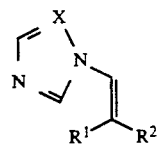

II where R$^1$, R$^2$ and X have the abovementioned meanings, with chlorine or bromine in the presence of a Lewis acid, eg. zinc chloride or zinc bromide.

The reaction is carried out in the presence or absence of a solvent or diluent, at from −30° to 100° C. The preferred solvents include, for example, esters, such as ethyl acetate, methyl acetate or butyl acetate, ethers, such as tetrahydrofuran, diethyl ether, dimethoxyethane, dioxane or diisopropyl ether, and in particular hydrocarbons and chlorohydrocarbons, such as pentane, hexane, benzene, methylene chloride, chloroform, carbon tetrachloride or dichloroethane, or corresponding mixtures.

Preferred Lewis acids are metal halides, eg. zinc chloride, zinc bromide, tin chloride, tin bromide, iron tribromide, aluminum trichloride or titanium tetrachloride.

The reaction is generally carried out at from −30° to 100° C, under atmospheric or superatmospheric pressure, continuously or batchwise.

The starting compounds II may be prepared, for example, by reacting a compound of the formula III

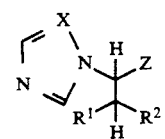

III where A, B, X and Z have the abovementioned meanings, with a base.

The reaction is carried out in the presence or absence of a solvent or diluent, with the addition of an inorganic or organic base and with or without the addition of a reaction accelerator, at from 10° to 150° C. The preferred solvents and diluents include ketones, such as acetone, methyl ethyl ketone or cyclohexanone, nitriles, such as acetonitrile or propionitrile, alcohols, such as methanol, ethanol, isopropanol, n-butanol or glycol, esters, such as ethyl acetate, methyl acetate or butyl acetate, ethers, such as tetrahydrofuran, diethyl ether, dimethoxyethane, dioxane or diisopropyl ether, and amides, such as dimethylformamide or N-methylpyrrolidone, as well as dimethyl sulfoxide, sulfolane and corresponding mixtures.

Suitable bases, which may also be used as acid acceptors in the reaction, are, for example, alkali metal hydroxides, such as lithium hydroxide, sodium hydroxide or potassium hydroxide, alkali metal carbonates, such as sodium carbonate or cesium carbonate, alkali metal hydrides, such as lithium hydride, sodium hydride or potassium hydride, alkali metal amides, such as sodium amide or potassium amide, and pyridine and 4-dimethylaminopyridine. However, it is also possible to use other conventional bases.

Preferred reaction accelerators are metal halides, such as sodium iodide or potassium iodide, and quaternary ammonium salts, such as tetrabutylammonium bromide or iodide.

However, the compounds of the formula II can also be prepared by known processes (cf. European Patent 60,223).

The compounds of the formula III can be prepared by reacting a compound of the formula IV

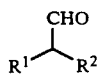
IV where $R^1$ and $R^2$ have the abovementioned meanings, with a compound of the formula V

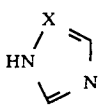
V where X has the abovementioned meaning, in the presence of an appropriate thionyl halide ($SOZ_2$).

The reaction is carried out in the presence or absence of a solvent or diluent, at from $-30°$ to $80°$ C. The preferred solvents and diluents include nitriles, such as acetonitrile or propionitrile, ethers, such as tetrahydrofuran, diethyl ether, dimethoxyethane, dioxane or diisopropyl ether, and in particular hydrocarbons and chlorohydrocarbons, such as pentane, hexane, toluene, methylene chloride, chloroform, carbon tetrachloride or dichloroethane, and corresponding mixtures.

The compounds of the formula IV can be prepared by generally known processes for aldehyde synthesis (Houben-Weyl-Muller, Methoden der Organischen Chemie, Georg Thieme Verlag, Stuttgart 1983, Vol. E3).

The compounds of the formula I can also be prepared by reacting a compound of the formula

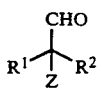

where $R^1$, $R^2$ and Z have the abovementioned meanings, with a compound of the formula

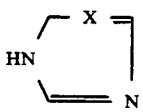

where X has the abovementioned meanings, in the presence of a thionyl halide ($SOZ_2$).

The reaction is carried out in the presence or absence of a solvent or diluent at from $-30°$ to $80°$ C. The preferred solvents and diluents include nitriles, such as acetonitrile or propionitrile, ethers, such as tetrahydrofuran, diethyl ether, dimethoxyethane, dioxane or diisopropyl ether, and in particular hydrocarbons and chlorohydrocarbons, such as pentane, hexane, toluene, methylene chloride, chloroform, carbon tetrachloride or dichloroethane, and corresponding mixtures.

The Examples which follow illustrate the preparation of the active ingredients.

I. PREPARATION OF THE STARTING MATERIALS METHOD 1

1-Chloro-1-(1,2,4-triazol-1-yl)-2-(2-fluorophenyl)-2-(4-fluorophenyl)-ethane 51.55 g of thionyl chloride are added to a solution of 119.6 g of triazole in 500 ml of dichloromethane at 0° C. After the end of the addition, the mixture is stirred for 30 minutes at room temperature (20° C), after which 67 g of 2-fluorophenyl-4-fluorophenylacetaldehyde are added. After the reaction mixture has been stirred for 12 hours at room temperature, 300 ml of water are added to the solution and the organic phase is separated off. The remaining aqueous phase is extracted twice by shaking with dichloromethane, and the collected organic phases are washed twice with saturated sodium bicarbonate solution. The organic phase separated off is then dried over sodium sulfate and evaporated down, 84.7 g (92%) of 1-chloro-1-(1,2,4-triazol-1-yl)-2-(2-fluorophenyl)-2-(4-fluorophenyl)-ethane being obtained as a 1:1 diastereomer mixture, in the form of an oil.

METHOD 2

1-(1,2,4-Triazol-1-yl)-2-(2-fluorophenyl)-2-(4-fluorophenyl)-ethene 28.6 g of sodium methylate and 0.2 g of potassium iodide are added to a solution of 84.7 g of 1-chloro-1(1,2,4-triazol-1-yl)-2-(2-fluorophenyl)-2-(4-fluorophenyl)-ethane in 500 ml of methanol. After the reaction mixture has been refluxed for one hour, 300 ml of water are added to the solution, which is extracted several times by shaking with methyl tert-butyl ether. The organic phase separated off is washed twice with water, then dried over sodium sulfate and evaporated down, 67 g (89%) of 1-(1,2,4-triazol-1-yl)-2-(2-fluorophenyl)-2-(4-fluorophenyl)-ethene being obtained in the form of an oil.

PREPARATION OF THE END PRODUCTS

EXAMPLE 1

1,2-Dichloro-1-(1,2,4-triazol-1-yl)-2-(2-fluorophenyl)-2-(4-fluorophenyl)-ethane (active ingredient No. 1)

1.1 g of zinc chloride are added to a solution of 22.4 g of 1-(1,2,4-triazol-1-yl)-2-(2-fluorophenyl)-2-(4-fluorophenyl)-ethene in 80 ml of carbon tetrachloride, after which 8.4 g of chlorine are passed in gaseous form. After the reaction mixture has been stirred for two hours at room temperature, the resulting precipitate is filtered off under suction and taken up in methylene chloride, and the solution is washed several times with saturated sodium bicarbonate solution, dried over sodium sulfate and evaporated down. 17.8 g (63%) of 1,2-dichloro-1-(1,2,4-triazol-1-yl)-2-(2-fluorophenyl)-2-(4-fluorophenyl)-ethane are obtained as a 1:1 diastereomer mixture.

The compounds listed in the Table can be prepared similarly to Example 1.

TABLE I

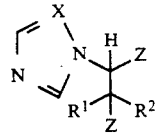

| Ex. | R¹ | R² | X | Z | m.p./IR | Isomer* |
|---|---|---|---|---|---|---|
| 1 | 4-F—C₆H₄ | 2-F—C₆H₄ | N | Cl | 1604, 1507, 1237, 816 754 cm⁻¹ | D₁:D₂ = 1:1 |
| 2 | 4-F—C₆H₄ | 2-F—C₆H₄ | CH | Cl | | |
| 3 | 4-F—C₆H₄ | 2-F—C₆H₄ | N | Br | 1602, 1509, 1226, 836 760 cm⁻¹ | D₁:D₂ = 1:1 |
| 4 | 4-F—C₆H₄ | 2-F—C₆H₄ | CH | Br | | |
| 5 | 4-F—C₆H₄ | 3-F—C₆H₄ | N | Cl | | |
| 6 | 4-F—C₆H₅ | 4-F—C₆H₄ | N | Cl | 127–129° C. | enantiomer mixture |
| 7 | 4-F—C₆H₄ | 4-F—C₆H₄ | CH | Cl | | |
| 8 | 4-F—C₆H₄ | 4-F—C₆H₄ | N | Br | | |
| 9 | 4-F—C₆H₄ | 4-F—C₆H₄ | CH | Br | | |
| 10 | 4-F—C₆H₄ | C₆H₅ | N | Cl | resin | D₁:D₂ = 1:1 |
| 11 | 4-F—C₆H₄ | C₆H₅ | N | Br | | |
| 12 | 4-F—C₆H₄ | C₆H₅ | CH | Cl | | |
| 13 | 4-F—C₆H₄ | 2-Cl—C₆H₄ | N | Cl | 1506, 1277, 1236, 816, 750 cm⁻¹ | D₁:D₂ = 1:1 |
| 14 | 4-F—C₆H₄ | 2-Cl—C₆H₄ | CH | Cl | | |
| 15 | 4-F—C₆H₄ | 2-Cl—C₆H₄ | N | Br | | |
| 16 | 4-F—C₆H₄ | 2-Cl—C₆H₄ | CH | Br | | |
| 17 | 4-F—C₆H₄ | 3-Cl—C₆H₄ | N | Cl | | |
| 18 | 4-F—C₆H₄ | 4-Cl—C₆H₄ | N | Cl | | |
| 19 | 4-F—C₆H₄ | 4-Cl—C₆H₄ | N | Br | | |
| 20 | 4-F—C₆H₄ | 4-Cl—C₆H₄ | CH | Cl | | |
| 21 | 4-F—C₆H₄ | 2-Br—C₆H₄ | N | Cl | | |
| 22 | 4-F—C₆H₄ | p-biphenyl | N | Cl | | |
| 23 | 4-F—C₆H₄ | 2-naphthyl | N | Cl | | |
| 24 | 4-F—C₆H₄ | 1-naphthyl | N | Cl | | |
| 25 | 4-F—C₆H₄ | 2-CH₃—C₆H₄ | N | Cl | | |
| 26 | 4-F—C₆H₄ | 2-CH₃—C₆H₄ | N | Br | | |
| 27 | 4-F—C₆H₄ | 2-CH₃—C₆H₄ | CH | Cl | | |
| 28 | 4-F—C₆H₄ | 4-CH₃—C₆H₄ | N | Cl | | |
| 29 | 4-F—C₆H₄ | 2,4-di-CH₃—C₆H₃ | N | Cl | | |
| 30 | 4-F—C₆H₄ | 2-CF₃—C₆H₄ | N | Cl | | |
| 31 | 4-F—C₆H₄ | 2-CF₃—C₆H₄ | N | Br | | |
| 32 | 4-F—C₆H₄ | 2-CF₃—C₆H₄ | CH | Cl | | |
| 33 | 4-F—C₆H₄ | 3-CF₃—C₆H₄ | N | Cl | | |
| 34 | 4-F—C₆H₄ | 4-CF₃—C₆H₄ | N | Cl | | |
| 35 | 4-F—C₆H₄ | 4-CF₃—C₆H₄ | N | Br | | |
| 36 | 4-F—C₆H₄ | 4-CF₃—C₆H₄ | CH | Cl | | |
| 37 | 4-F—C₆H₄ | 3-NO₂—C₆H₄ | N | Cl | | |
| 38 | 4-F—C₆H₄ | 3-NH₂—C₆H₄ | N | Cl | | |
| 39 | 4-F—C₆H₄ | 2-OCH₃—C₆H₄ | N | Cl | | |
| 40 | 4-F—C₆H₄ | 2-OCH₃—C₆H₄ | N | Br | | |
| 41 | 4-F—C₆H₄ | 2-OCH₃—C₆H₄ | CH | Cl | | |
| 42 | 4-F—C₆H₄ | 3-OCH₃—C₆H₄ | N | Cl | | |
| 43 | 4-F—C₆H₄ | 3-OCH₃—C₆H₄ | N | Br | | |
| 44 | 4-F—C₆H₄ | 4-OCH₃—C₆H₄ | N | Cl | | |
| 45 | 4-F—C₆H₄ | 4-OCH₃—C₆H₄ | N | Br | | |
| 46 | 4-F—C₆H₄ | 4-OCH₃—C₆H₄ | CH | Cl | | |
| 47 | 4-F—C₆H₄ | 2-pyridyl | N | Cl | | |
| 48 | 4-F—C₆H₄ | 3-pyridyl | N | Cl | | |
| 49 | 4-F—C₆H₄ | 4-pyridyl | N | Cl | | |
| 50 | 4-F—C₆H₄ | 2-thienyl | N | Cl | | |
| 51 | 4-F—C₆H₄ | 3-thienyl | N | Cl | | |
| 52 | 4-F—C₆H₄ | 2-furyl | N | Cl | | |
| 53 | 4-F—C₆H₄ | 5-isoxazolyl | N | Cl | | |
| 54 | C₆H₅ | 2-F—C₆H₄ | N | Cl | | |
| 55 | C₆H₅ | C₆H₅ | N | Cl | | |
| 56 | C₆H₅ | 2-Cl—C₆H₄ | N | Cl | 1502, 1277, 1133, 752 cm⁻¹ | D₁:D₂ = 1:1 |
| 57 | C₆H₅ | 4-Cl—C₆H₄ | N | Cl | 1494, 1276, 1096, 1014 756, 701 cm⁻¹ | D₁:D₂ = 1:1 |
| 58 | C₆H₅ | 2-Br—C₆H₄ | N | Cl | | |
| 59 | C₆H₅ | 4-Br—C₆H₄ | N | Cl | | |
| 60 | C₆H₅ | 2-CH₃—C₆H₄ | N | Cl | | |
| 61 | C₆H₅ | 4-CH₃—C₆H₄ | N | Cl | | |
| 62 | C₆H₅ | 4-tert.-C₄H₉—C₆H₄ | N | Cl | | |
| 63 | C₆H₅ | 2-CF₃—C₆H₄ | N | Cl | | |
| 64 | C₆H₅ | 4-CF₃—C₆H₄ | N | Cl | | |
| 65 | C₆H₅ | 2-OCH₃—C₆H₄ | N | Cl | | |
| 66 | C₆H₅ | 4-OCH₃—C₆H₄ | N | Cl | | |
| 67 | C₆H₅ | 2-naphthyl | N | Cl | | |
| 68 | C₆H₅ | 2-pyridyl | N | Cl | | |
| 69 | C₆H₅ | 3-pyridyl | N | Cl | | |

TABLE-continued

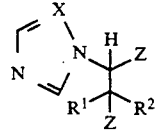

I

| Ex. | R¹ | R² | X | Z | m.p./IR | Isomer* |
|---|---|---|---|---|---|---|
| 70 | C₆H₅ | 2-thienyl | N | Cl | | |
| 71 | C₆H₅ | 3-thienyl | N | Cl | | |
| 72 | 4-Cl—C₆H₄ | 2-F—C₆H₄ | N | Cl | | |
| 73 | 4-Cl—C₆H₄ | 2-Cl—C₆H₄ | N | Cl | | |
| 74 | 4-Cl—C₆H₄ | 4-Cl—C₆H₄ | N | Cl | 1502, 1490, 831, 764 cm⁻¹ | enantiomer mixture |
| 75 | 4-Cl—C₆H₄ | 2-Br—C₆H₄ | N | Cl | | |
| 76 | 4-Cl—C₆H₄ | 4-Br—C₆H₄ | N | Cl | | |
| 77 | 4-Cl—C₆H₄ | 2-CH₃—C₆H₄ | N | Cl | | |
| 78 | 4-Cl—C₆H₄ | 4-CH₃—C₆H₄ | N | Cl | | |
| 79 | 4-Cl—C₆H₄ | 2-CF₃—C₆H₄ | N | Cl | | |
| 80 | 4-Cl—C₆H₄ | 4-CF₃—C₆H₄ | N | Cl | | |
| 81 | 4-Cl—C₆H₄ | 2-OCH₃—C₆H₄ | N | Cl | | |
| 82 | 4-Cl—C₆H₄ | 4-OCH₃—C₆H₄ | N | Cl | | |
| 83 | 4-Br—C₆H₄ | 2-F—C₆H₄ | N | Cl | | |
| 84 | 4-Br—C₆H₄ | 2-Cl—C₆H₄ | N | Cl | | |
| 85 | 4-Br—C₆H₄ | 2-CH₃—C₆H₄ | N | Cl | | |
| 86 | 4-Br—C₆H₄ | 2-CF₃—C₆H₄ | N | Cl | | |
| 87 | 4-Br—C₆H₄ | 4-CF₃—C₆H₄ | N | Cl | | |
| 88 | 4-Br—C₆H₄ | 2-OCH₃—C₆H₄ | N | Cl | | |
| 89 | 4-Br—C₆H₄ | 4-OCH₃—C₆H₄ | N | Cl | | |
| 90 | 4-CH₃—C₆H₄ | 2-Cl—C₆H₄ | N | Cl | | |
| 91 | 4-CH₃—C₆H₄ | 2-F—C₆H₄ | N | Cl | | |
| 92 | 4-CH₃—C₆H₄ | 2-CH₃—C₆H₄ | N | Cl | | |
| 93 | 4-CH₃—C₆H₄ | 4-CH₃—C₆H₄ | N | Cl | | |
| 94 | 4-CH₃—C₆H₄ | 2-CF₃—C₆H₄ | N | Cl | | |
| 95 | 4-CH₃—C₆H₄ | 4-CF₃—C₆H₄ | N | Cl | | |
| 96 | 4-CH₃—C₆H₄ | 2-OCH₃—C₆H₄ | N | Cl | | |
| 97 | 4-CH₃—C₆H₄ | 4-OCH₃—C₆H₄ | N | Cl | | |
| 98 | 4-CF₃—C₆H₄ | 2-Cl—C₆H₄ | N | Cl | | |
| 99 | 4-CF₃—C₆H₄ | 2-F—C₆H₄ | N | Cl | | |
| 100 | 4-CF₃—C₆H₄ | 2-CH₃—C₆H₄ | N | Cl | | |
| 101 | 4-CF₃—C₆H₄ | 2-CF₃—C₆H₄ | N | Cl | | |
| 102 | 4-CF₃—C₆H₄ | 2-OCH₃—C₆H₄ | N | Cl | | |
| 103 | 4-OCH₃—C₆H₄ | 2-Cl—C₆H₄ | N | Cl | | |
| 104 | 4-OCH₃—C₆H₄ | 2-F—C₆H₄ | N | Cl | | |
| 105 | 4-OCH₃—C₆H₄ | 2-CH₃—C₆H₄ | N | Cl | | |
| 106 | 4-OCH₃—C₆H₄ | 2-CF₃—C₆H₄ | N | Cl | | |
| 107 | 4-OCH₃—C₆H₄ | 2-OCH₃—C₆H₄ | N | Cl | | |
| 108 | 4-OCH₃—C₆H₄ | 4-OCH₃—C₆H₄ | N | Cl | | |
| 109 | 2-F—C₆H₄ | 2-Cl—C₆H₄ | N | Cl | | |
| 110 | 2-F—C₆H₄ | 2-F—C₆H₄ | N | Cl | | |
| 111 | 2-F—C₆H₄ | 2-CH₃—C₆H₄ | N | Cl | | |
| 112 | 2-Cl—C₆H₄ | 2-CH₃—C₆H₄ | N | Cl | | |
| 113 | 2-Cl—C₆H₄ | 2-CF₃—C₆H₄ | N | Cl | | |
| 114 | 2-Cl—C₆H₄ | 2-OCH₃—C₆H₄ | N | Cl | | |

*D₁:D₂ = ratio of the diastereomers formed

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia species in cotton and lawns,
Rhizoctonia species in cotton and lawns,
Ustilago species in cereals and sugar cane,
Venturia inaequalis (scab) in applies,
Helminthosprium species in cereals,
Septroria nodrum in wheat,
Botrytis cinerea (gray mold) in strawberries and grapes,
Cercospora arachidicola in groundnuts,
Pseudocercosproella herpotrichoides in wheat and barley, Pyricularia oryzae in rice,
Phytophthora infestans in potatoes and tomatoes,
Fusarium and Verticillium species in various plants,
Plasmopara viticola in grapes,
Alternaria species in vegetables and fruit.

The compounds are applied by spraying or dusting the plants with the active ingredients, or treating the seeds of the plants with the active ingredients. They may be applied before or after infection of the plants or seeds by the fungi.

Application rates of the fungicidal agents are from 0.02 to 3 kg or ore of active ingredient per hectare, depending on the type of effect desired. The novel compounds may also be used for protecting materials (wood), for example against Paecilomyces variotii.

The novel compounds may exercise a variety of influences on practically all plant development stages and are therefore used as growth regulators. The diversity of action of growth regulators depends especially on
(a) the type and variety of plant;
(b) the time applied with reference to the development stage of the plants and the time of the Year;
(c) the place and method of application seed treatment, soil treatment, or application to foliage;
(d) climatic factors, e.g., average temperature, amount of precipitate, sunshine and duration;
(e) soil conditions (including fertilization;
(f) the formulation of the active ingredient; and
(g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges canal embankments and on areas such as parks, sportsgrounds, fruit orchards, lawns and airfields, thus reducing expensive and time-consuming mowing.

A further feature of economic interest is the increase in the rigor of crops which tend to lodge such as cereals, Indian corn, sunflowers and soybeans. The shortening and strengthening of the stem thus caused reduces or eliminates the danger of lodging under unfavorable weather conditions.

Of practical importance is the reduction in vegetative growth in fruit trees and other woody plants, thus saving pruning costs.

The use of growth regulators and also so important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development. with the novel compounds, it is possible for instance in winter rape to considerably increase the resistance to freeze injury. On the one hand, upward growth and the development of a too luxuriant (and thus particularly frost-susceptible) leaf or plant mass are inhibited; on the other, the Young rape plants are kept in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a Preventive measure against increased susceptibility to freeze injury and—because of the relatively low leaf or plant mass—attach by various (especially fungus) diseases. The inhibition of vegetative growth also makes closer planting possible in numerous crops, which means an increase in yield based on the area cropped.

B. Better yields both of plant parts and plant materials may be obtained with the novel agents. It is thus for instance possible to induce increased formation of buds blossom leaves, fruit, seed grains, roots and tubers, to increase the sugar content of sugarbeets, sugarcane and citrus fruit, to raise the protein content of cereals and soybeans, and to stimulate the increased formation of latex in rubber trees.

The compounds of the formula I may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism. i.e.. promotion of the formation of separation layers between fruit or leaf and stem of the plant is also essential for a readily controllable defoliation of crop plants e.g., cotton.

D. Further, transpiration in crop plants may be reduced with growth regulators. This is particularly important for plants growing in agricultural areas which are expensive to irrigate. e.g.. in arid or semi-arid areas. Irrigation frequency can be reduced by using the compounds according to the invention, making for lower costs. As a result of the use of growth regulators, the water available can be better utilized because inter alia,
the size of the stomata opening is reduced:
a thicker epidermis and cuticle are formed:
penetration of the soil by the roots is improved:
the micro-climate in the stand is favorably influenced by the more compact growth.

The active ingredients according to the invention may be applied not only to the seed (as a disinfectant), but also to the soil, i.e., via the roots, and to the foliage by spraying.

As a result of the good tolerance by crop plants, the application rate when the active ingredients are used as growth regulators may vary within wide limits.

When the active ingredients are used for treating seed, amounts of from 0.001 to 50, and preferably from 0.005 to 0.5, per kg of seed are generally required. For foliage and soil treatment, amounts of from 0.01 to 10, and preferably from 0.05 to 1, kg/ha are generally considered to be sufficient.

The novel substances may be converted into conventional formulations such as solutions, emulsions, suspensions, dusts, powders, pastes and granules. The application forms depend entirely on the purposes for which they are intended: they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics e.g., chlorobenzenes, paraffins (e.g., crude oil fractions), alcohols e.g., methanol, butanol), amines (e.g. ethanolamine, dimethylformamide), and water; carriers such as ground natural minerals (e.g., kaolins, aluminas, talc and chalk) and around synthetic minerals (e.g., highly disperse silica and silicates); emulsifiers and other surfactants, such as nonionic and anionic emulsifiers (e.g., polyoxyethylene fatty alcohol ethers, alkyl sulfonates); and dispersants such as lignin, sulfite waste liquors and methylcellulose.

The fungicidal agents generally contain from 0.1 to 95, and preferably from 0.5 to 90, wt % of active ingredient.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 13 is mixed with 10 parts by weight of N-methyl-α-pyrrolidone. A mixture is obtained which is suitable for application in the form of very fine drops.

II. 20 parts by weight of compound no. 13 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 13 is dissolved in a mixture consisting of 40 parts by weight of cyclohexanone, 30 parts by weight of isobutanol, 20 parts by weight of the adduct of 40 moles of ethylene oxide and b 1 mole of castor oil. By pouring the solution into water and finely distributing it therein, an aqueous dispersion is obtained.

IV. 20 parts by weight of compound no. 13 id dissolved in a mixture consisting of 25 parts by weight of cyclohexanol, 65 parts by weight of a mineral oil fraction having a boiling point between 210° C. and 280° C., and 10 parts by weight of the adduct of 40 moles of ethylene oxide and b 1 mole of castor oil. By pouring the solution into water and uniformly distributing it therein, an aqueous dispersion is obtained.

V. 80 parts by weight of compound no. 13 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 13 is intimately mixed with 97 parts by weight of particulate kaolin. A dust is obtained containing 3% by weight of the active ingredient.

VII. 30 parts by weight of compound no. 13 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 13 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 13 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

USE EXAMPLES

For comparison purposes, the compound 2,4'-difluoro-α-(1,2,4-triazol-1-yl-methyl)-benzhydryl alcohol (A) disclosed in EP 15,756 was used.

USE EXAMPLE

Action on Pyrenophora trees

Barley seedlings of the "Igri" variety were sprayed to runoff at the two-leaf stage with aqueous suspensions consisting (dry basis) of 80% of active ingredient and 20% of emulsifier. After 24 hours of plants were inoculated with a spore suspension of the fungus Pyrenophora trees, and set up for 48 hours in a high-humidity climatic cabinet at 18° C. The plants were then cultivated for a further 5 days in the greenhouse at 20° to 22° C. and a relative humidity of 70° C. The extent of fungus spread was then assessed.

The results show that active ingredient 13, applied as a 0.0125 wt % spray liquor, has a better fungicidal action (100%) than prior art comparative agent A (80%).

To determine the growth-regulating properties of the candidate compounds, the test plants were grown in plastic pots (approx. 12.5 cm in diameter, and having a volume of about 500 ml) in a substrate provided with sufficient nutrients.

In the preemergence treatment method, the candidate compounds were sprayed as aqueous formulations onto the seedbed on the day of sowing. In the postemergence method, the compounds were sprayed as aqueous formulations onto the plants.

The growth-regulating action observed was confirmed at the end of the experiment by measuring the height of the plants. The figures obtained were compared with the growth height of the untreated plants. The active ingredient CCC was used for comparison purposes.

The reduction in growth height was also accompanied by a deeper leaf coloration. The increased chlorophyll content is indicative of an increased rate of photosynthesis, making for bigger yields.

The individual data are given in the following tables.

Comparative substances:

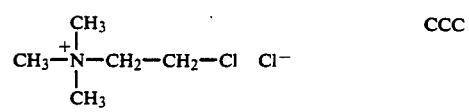

CCC

TABLE 1

| | Spring rape, "Petranova" variety Preemergence (soil) treatment | |
|---|---|---|
| Active ingr. no. | Conc. mg of a.i./vessel | Growth height relative |
| untreated | — | 100 |
| CCC | 6 | 95.9 |
| 6 | 6 | 91.3 |
| 10 | 6 | 88.7 |

TABLE 2

| | Spring rape, "Petranova" variety Postemergence (leaf) treatment | |
|---|---|---|
| Active ingr. no. | Conc. mg of a.i./vessel | Growth height relative |
| untreated | — | 100 |
| CCC | 6 | 92.2 |
| 1 | 6 | 88.3 |
| 10 | 6 | 84.4 |
| 74 | 6 | 75.6 |

We claim:

1. A compound selected from the group consisting of those having the formula I

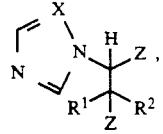

where $R^1$ and $R^2$ are identical or different and each is phenyl, biphenyl, or naphthyl and these radicals may be nomo to tri-substituted by halogen, nitro, phenoxy, amino, alkyl, alkoxy or haloalkyl, each of 1 to 4 carbon atoms, Z is chlorine or bormine, and X is N, and their plant-tolerated acid addition salts and metal complexes.

2. A fungicidal composition containing a carrier and a fungicidally effective amount of a compound of the formula I according to claim 1, or a plant tolerated acid addition salt or metal complex thereof.

3. A process for combating fungi, wherein a fungicidally effective amount of a compound of formula I according to claim 1, or a plant-tolerated acid addition salt or metal complex thereof, is allowed to act on the fungi or the plant materials, plant areas, plants or seed threatened by fungus attack.

4. A compound according to claim 1 wherein $R^1$ is phenyl, $R^2$ is 2-chlorophenyl, and Z is chlorine.

5. A compound of claim 1 wherein $R^1$ is phenyl, $R^2$ is 4-chlorophenyl, and Z is chlorine.

6. A compound of claim 1 wherein $R^1$ is 4-fluorophenyl, $R^2$ is 2-fluorophenyl, and Z is chlorine.

* * * * *